(12) United States Patent
Kim et al.

(10) Patent No.: US 9,067,970 B2
(45) Date of Patent: Jun. 30, 2015

(54) ANTICANCER AGENTS COMPRISING PEPTIDES WITH CANCER-SPECIFIC TOXICITY

(75) Inventors: Sun Chang Kim, Daejeon (KR); Su A Jang, Daejeon (KR); Da Jung Kim, Daejeon (KR); Bong Hyun Sung, Daejeon (KR); Ki Jeong Lim, Daejeon (KR); Ju Ri Shin, Daejeon (KR); Young Woong Lee, Daejeon (KR)

(73) Assignees: Korea Advanced Institute of Science and Technology, Daejeon (KR); Intelligent Synthetic Biology Center, Daejeon (KR)

( * ) Notice: Subject to any disclaimer, the term of this patent is extended or adjusted under 35 U.S.C. 154(b) by 0 days.

(21) Appl. No.: 13/700,722

(22) PCT Filed: Dec. 24, 2010

(86) PCT No.: PCT/KR2010/009303
§ 371 (c)(1),
(2), (4) Date: Apr. 29, 2013

(87) PCT Pub. No.: WO2011/149173
PCT Pub. Date: Dec. 1, 2011

(65) Prior Publication Data
US 2013/0244949 A1 Sep. 19, 2013

(30) Foreign Application Priority Data

May 28, 2010 (KR) .................. 10-2010-0050461

(51) Int. Cl.
*G01N 33/574* (2006.01)
*A61K 38/10* (2006.01)
*C07K 7/08* (2006.01)
*G01N 33/53* (2006.01)

(52) U.S. Cl.
CPC *C07K 7/08* (2013.01); *G01N 33/53* (2013.01); *G01N 33/574* (2013.01); *A61K 38/10* (2013.01)

(58) Field of Classification Search
CPC ... A61K 2300/00; A61K 38/08; A61K 38/10; A61K 38/1709; A61K 2035/124; A61K 33/24; A61K 38/00; A61K 45/06; A61K 47/186; A61K 48/00; A61K 9/0014; A61K 9/0019; A61K 9/1272; G01N 33/534; G01N 33/574; G01N 33/743; G01N 33/76
See application file for complete search history.

(56) References Cited

U.S. PATENT DOCUMENTS 6,720,413 B1 4/2004 Schweinfest et al.
6,946,133 B1 9/2005 Schlom et al.
(Continued)

FOREIGN PATENT DOCUMENTS

KR    836596 B1 * 7/2008

OTHER PUBLICATIONS

Freshney (Culture of Animal Cells, A Manual of Basic Technique, Alan R. Liss, Inc., 1983, New York, p. 3-4).*
(Continued)

*Primary Examiner* — Padma V Baskar
(74) *Attorney, Agent, or Firm* — Cooley LLP

(57) ABSTRACT

The present invention relates a prophylactic or therapeutic composition for cancer, and more particularly, to a prophylactic or therapeutic composition for cancer comprising a peptide which is represented by an amino acid sequence of the following Formula (I), a method for preventing or treating cancer comprising the step of administering the peptide to a subject, and use of the peptide in the preparation of the prophylactic or therapeutic composition for cancer. (I) APKAMX$^1$LLX$^2$X$^3$L-LX$^4$LQKKGI wherein X$^1$, X$^2$, X$^3$ and X$^4$ are each independently R or K.

3 Claims, 10 Drawing Sheets

(56) References Cited

U.S. PATENT DOCUMENTS 7,601,693 B2    10/2009    Yang et al.
2009/0197798 A1  8/2009    Yang et al.

OTHER PUBLICATIONS

Dermer (Bio/Technology, 1994, 12:320).*

Gura (Science, v278, 1997, pp. 1041-1042).*

Simone, Oncology: Introduction, Cecil Textbook of Medicine, 1996, 20th Edition, vol. 1, pp. 1004-1010.*

Park et al., "Helix Stability Confers Salt Resistance upon Helical Antimicrobial Peptides," The Journal of Biological Chemistry 279(14): 13896-13901, 2004.

* cited by examiner

SEQUENCE LISTING

```
<160> NUMBER OF SEQ ID NOS: 2

<210> SEQ ID NO 1
<211> LENGTH: 19
<212> TYPE: PRT
<213> ORGANISM: Artificial Sequence
<220> FEATURE:
<223> OTHER INFORMATION: NKC peptide

<400> SEQUENCE: 1

Ala Pro Lys Ala Met Lys Leu Leu Lys Lys Leu Leu Lys Leu Gln Lys
 1               5                  10                  15

Lys Gly Ile

<210> SEQ ID NO 2
<211> LENGTH: 19
<212> TYPE: PRT
<213> ORGANISM: Artificial Sequence
<220> FEATURE:
<223> OTHER INFORMATION: NRC peptide

<400> SEQUENCE: 2

Ala Pro Lys Ala Met Arg Leu Leu Arg Arg Leu Leu Arg Leu Gln Lys
 1               5                  10                  15

Lys Gly Ile
```

ANTICANCER AGENTS COMPRISING PEPTIDES WITH CANCER-SPECIFIC TOXICITY

CROSS-REFERENCES TO RELATED APPLICATIONS

This application is a U.S. national phase application of International PCT Patent Application No. PCT/KR2010/009303, which was filed on Dec. 24, 2010, which claims priority to Korean Patent Application No. 10-2010-0050461, filed May 28, 2010. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_020_01US_ST25.txt. The text file is 1 KB, was created on Nov. 28, 2012, and is being submitted electronically via EFS-Web.

TECHNICAL FIELD

The present invention relates a prophylactic or therapeutic composition for cancer, and more particularly, to a prophylactic or therapeutic composition for cancer comprising a peptide which is represented by an amino acid sequence of the following Formula (I), a method for preventing or treating cancer comprising the step of administering the peptide to a subject, and use of the peptide in the preparation of the prophylactic or therapeutic composition for cancer.

$$APKAMX^1LLX^2X^3LLX^4LQKKGI \quad (I)$$

wherein $X^1$, $X^2$, $X^3$ and $X^4$ are each independently R or K.

BACKGROUND ART

The present invention relates to a peptide having an anticancer activity. In particular, the present invention relates to a peptide showing a strong anticancer activity on hematologic malignancies as well as various carcinomas including skin cancer, cervical cancer, lung cancer, rectal cancer, and prostate cancer.

Most of the anticancer agents currently used have been developed by chemotherapy, and their pharmacological actions vary depending on the type of cancer (The pharmacological Basis of therapeutics, 18:1202, 1986), and many side effects due to toxicity of anticancer agents are the central problem in cancer treatment (Wonkwang Medical Sci. 3:13-34, 1987). In addition, anticancer agents effectively suppress the growth of cancer cells, whereas on occasion they penetrate into the normal tissue, and causes damage to normal tissue, in particular, to actively dividing cells. Thus, anticancer agents cause bone marrow depression, digestive disorders, and hair loss, and cancer cells also undergo mutations during growth, proliferation and metastasis so as to acquire resistance to anticancer agents, which generate severe problems in cancer treatment. Therefore, there is an urgent need for the development of effective anticancer agents to prevent such severe problems including toxicity to normal cells and drug resistance of cancer cells.

Since anticancer agents using antimicrobial peptides target substances that are different from the known anticancer agents, and enhance intracellular delivery and effects of other anticancer agents, they can be advantageously used in combination with other anticancer agents. At present, anticancer drug market exceeds 63 hundred million dollars annually, and annual research expenses relating to anticancer drugs reach 15 hundred million dollars. According to a pharmaceutical market analysis company, Datamonitor, annual sales of therapeutic peptides/proteins in 2010 are estimated to reach 590 hundred million dollars, resulted in a two-fold increase than that in 2001. Despite the promising prospects, antimicrobial peptides as an anticancer agent are still under the research phase, and are not yet commercialized. Thus, development of antimicrobial peptides as anticancer agents is a preoccupation of the anticancer drug market.

In addition to the function of the natural defense against invading pathogens, other functions of antimicrobial peptides have been recently revealed. In particular, many reports have been made on the anticancer activities of BMAP-28, HNP-1 (β-defensin), lactoferricin B, LL-37, magainin 2, melittin, tachyplesin I in the cell membranes. In Korea, antimicrobial peptides such as Gaegurin 5, Gaegurin 6, Kaisin I, and Kaisin II were reported to inhibit the growth of cancer cells in vivo. According to the current reports, the inability of antimicrobial peptides to distinguish cancer cells from normal cells, when injected to an organism having growing cancer cells, is a significant drawback. As an anticancer agent, the use of antimicrobial peptides with small size and strong anticancer activity is expected to usher in a new stage of the development of anticancer agents. Therefore, there is a continuous need to develop antimicrobial peptides which are able to distinguish cancer cells from normal cells and act only on cancer cells.

DISCLOSURE OF INVENTION

Technical Problem

The present inventors have developed antimicrobial peptides which exhibit strong antimicrobial activity under high salt conditions against a wide variety of microorganisms including Gram-positive and Gram-negative bacteria and fungi, the antimicrobial activity is more excellent than those of the known antimicrobial peptides, disclosed in Korean Patent No. 0836596. From derivatives of the antimicrobial peptides, they also investigated peptides which are able to distinguish cancer cells from normal cells to selectively act only on cancer cells without affecting normal mammalian cells. In detail, they investigated the peptides which exhibit marked anticancer activities on hematologic malignancies as well as various carcinomas including skin cancer, cervical cancer, lung cancer, rectal cancer, and prostate cancer, thereby completing the present invention.

Solution to Problem

It is an object of the present invention to provide a prophylactic or therapeutic composition for cancer, comprising a peptide which is represented by an amino acid sequence of the following Formula (I):

$$APKAMX^1LLX^2X^3LLX^4LQKKGI \quad (I)$$

wherein $X^1$, $X^2$, $X^3$ and $X^4$ are each independently R or K.

It is another object of the present invention to provide a method for preventing or treating cancer, comprising the step of administering the peptide to a subject.

It is still another object of the present invention to provide use of the peptide represented by an amino acid sequence of the following Formula (I) in the preparation of the prophylactic or therapeutic composition for cancer.

Advantageous Effects of Invention

The prophylactic or therapeutic composition for cancer comprising the anticancer peptide of the present invention exhibits excellent cell selectivity by reducing the viability of cancer cells without affecting normal cells, thereby being effectively used as an active ingredient of safer anticancer agents.

BEST MODE FOR CARRYING OUT THE INVENTION

Figure 1:
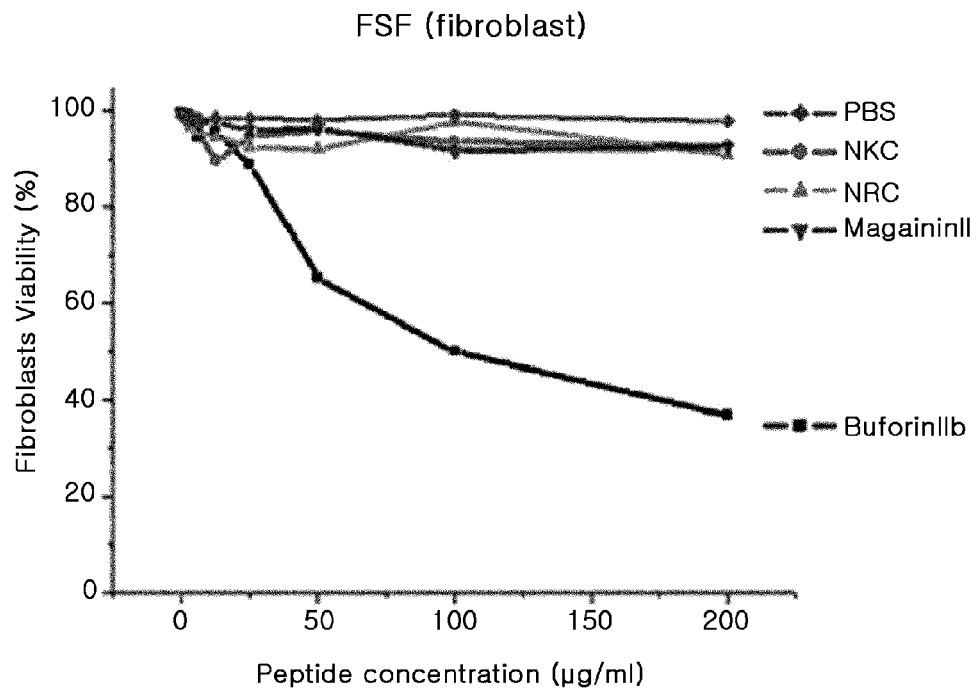
FIG. 1 is a graph showing the viability of FSF cells depending on the treatment concentration of the peptide.

In one aspect, the present invention relates to a prophylactic or therapeutic composition for cancer, comprising a peptide which is represented by an amino acid sequence of the following Formula (I):

$$APKAMX^1LLX^2X^3LLX^4LQKKGI \quad (I)$$

wherein $X^1$, $X^2$, $X^3$ and $X^4$ are each independently R or K.

The term "peptide", as used herein, means a polymer of amino acids joined together via an amide bond (or peptide bond). For the purpose of the present invention, the peptide means a peptide having high selectivity to cancer cells and strong anticancer activity. Preferably, the anticancer peptide of the present invention has the above Formula (I), wherein $X^1$, $X^2$, $X^3$ and $X^4$ are each independently a basic amino acid, R or K. The above Formula (I) contains a motif of X-LL-X, which is a motif constituting α-helix structure as a basic structure, and $X^1LLX^2X^3LLX^4$ corresponds to an extended α-helix structure of the motif repeats. More preferably, the anticancer peptide of the present invention may be a peptide represented by the amino acid sequence, SEQ ID NO. 1 of APKAMKLLKKLLKLQKKGI-amide or a peptide represented by the amino acid sequence, SEQ ID NO. 2 of APKA-MRLLRRLLRLQKKGI-amide.

The peptide of the present invention may further include a targeted sequence, a tag, a labeled residue, or an additional amino acid sequence designed to achieve the specific purpose of improving half-life or stability of the peptide. In addition, the peptide of the present invention may be linked to a coupling partner such as an effector molecule, a drug, a prodrug, a toxin, a peptide, and a carrier molecule.

The peptide of the present invention may be prepared by various methods widely known in the art. In detail, the peptide of the present invention may be prepared using genetic recombination and a protein expression system, or prepared in vitro by a chemical synthetic method such as peptide synthesis, or prepared by a cell-free protein synthetic method.

The peptide of the present invention may be prepared in the form of any pharmaceutically acceptable salt. Specifically, the peptide of the present invention can form a salt by addition of an acid, for examples, an inorganic acid (e.g., hydrochloric acid, hydrobromic acid, phosphoric acid, nitric acid, sulfuric acid, etc.) or organic carboxylic acid (e.g., acetic acid, haloacetic acid such as trifluoroacetic acid, propionic acid, maleic acid, succinic acid, malic acid, citric acid, tartaric acid, salicylic acid, etc.), acidic saccharide (e.g., glucuronic acid, galacturonic acid, gluconic acid and ascorbic acid), acidic polysaccharide (e.g., hyaluronic acid, chondroitin sulfate and alginic acid), organic sulfonic acid containing sugar ester sulfate such as chondroitin sulfate (e.g., methanesulfonic acid, p-toluenesulfonic acid) and so forth.

The peptide included in the prophylactic or therapeutic composition for cancer of the present invention is able to retain a stable activity at a high salt concentration due to a capping motif contained at N- and C-terminus. That is, the anticancer peptides of the present invention, represented by SEQ ID NO. 1 and SEQ ID NO. 2, contain an N-terminal fragment (APKAM) and a C-terminal fragment (LQKKGI) which have a predetermined sequence as a capping motif. Thus, the capping motif ensures structural stability of the secondary structure of the entire peptide irrespective of surrounding salt concentration. Such characteristic compensates for the structural weakness that antimicrobial peptides are easily degraded in vivo. Thus, it is very advantageous in the formulation of physiologically active peptides. Therefore, the present inventors have conducted continuous research to find a novel anticancer peptide represented by SEQ ID NO. 1 or SEQ ID NO. 2, which exhibits excellent anticancer activity but does not affect normal cells. In the present invention, the peptide was designated as NKC or NRC.

The term "cancer", as used herein, may include lung cancer bladder cancer, breast cancer, intestine cancer, kidney cancer, rectal cancer, liver cancer, brain cancer, esophagus cancer, gall-bladder cancer, ovarian cancer, pancreatic cancer, stomach cancer, cervical cancer, thyroid cancer, prostate cancer and skin (including squamous cell carcinoma) carcinomas and hematologic malignancies; mesenchymal tumors including fibrosarcoma and rhabdomyosarcoma; tumors in the central and peripheral nervous systems including astrocytoma, neuroblastoma, glioma and schwanoma; and other tumors including melanoma, seminoma, teratoma, osteosarcoma, xeroderma pigmentosum, keratoacanthoma, thyroid follicular carcinoma and Kaposi's sarcoma, and preferably skin cancer, cervical cancer, lung cancer, rectal cancer, and prostate cancer or hematologic malignancies.

The term "prevention", as used herein, means all of the actions in which the occurrence of cancer is restrained or retarded by administration of the composition.

The term "treatment", as used herein, means all of the actions in which cancer has taken a turn for the better or been modified favorably by administration of the composition.

The composition of the present invention may be preferably applied to a human, and also applied to livestock including cattle, horses, sheep, pigs, goats, camels, antelopes, dogs, and cats, which may suffer from inflammatory diseases or cancer and of which cancer can be restrained or reduced by administration of the peptide of the present invention.

The composition of the present invention may include one or more peptides represented by an amino acid sequence of the following Formula (I):

$$APKAMX^1LLX^2X^3LLX^4LQKKGI \qquad (I)$$

wherein $X^1$, $X^2$, $X^3$ and $X^4$ are each independently R or K.

The peptide may include other compounds, such as sugar chains, lipids, nucleic acids, other peptides or proteins. For example, the lipid compounds may be exemplified by dipalmitoylphosphatidylcholine (DPPC), palmitoyloleylphosphatidyl-glycerol (POPG), phosphatidylglycerol (PG), C18 saturated fatty acids, C16 unsaturated fatty acids and C18 unsaturated fatty acids.

Figure 2:
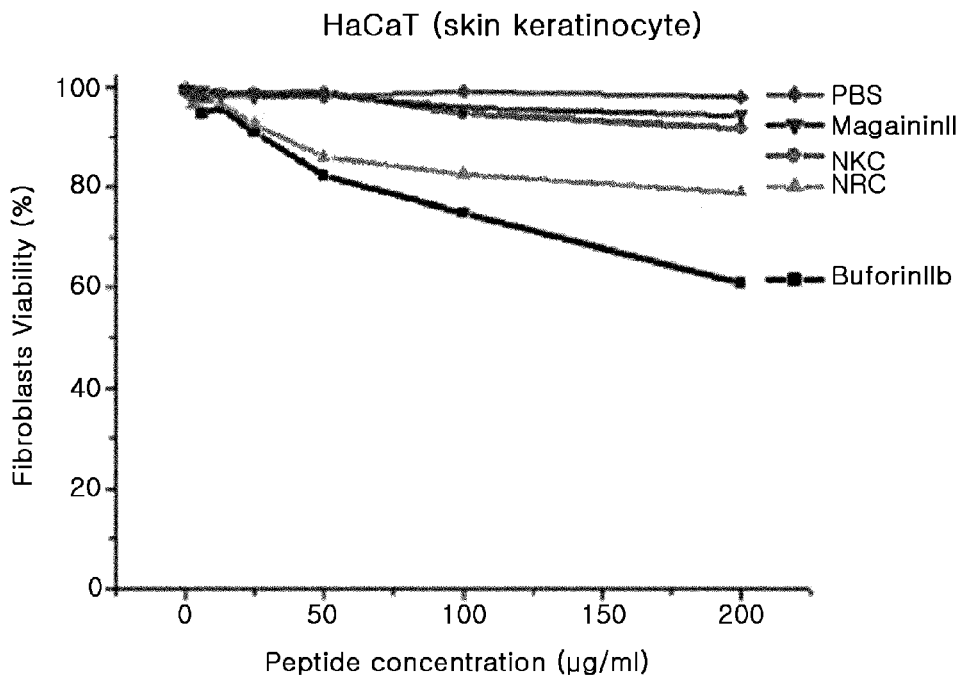
FIG. 2 is a graph showing the viability of HaCat cells depending on the treatment concentration of the peptide.
Figure 3:
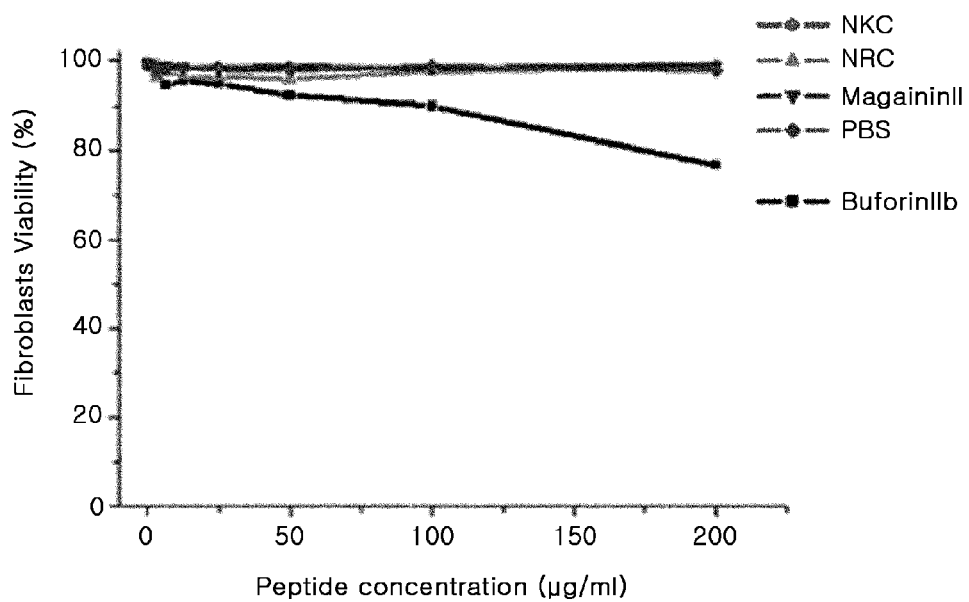
FIG. 3 is a graph showing the viability of erythrocytes depending on the treatment concentration of the peptide.

In accordance with one specific embodiment, MTT assay was performed to test the toxicity of NKC and NRC on normal cells in vitro. As a result, it was found that NKC and NRC exhibited little toxicity on normal cells, whereas buforin IIb, of which anticancer activity was previously reported, exhibited toxicity on normal cells (FIGS. 1 to 3). MTT assay was performed to test the anticancer activity of NKC and NRC against a variety of cancer cells in vitro. As a result, it was found that NKC and NRC exhibited very strong anticancer activity against various cancer cells including skin cancer cells, cervical cancer cells, lung cancer cells, rectal cancer cells, prostate cancer cells, and hematologic malignant cells, in vitro (FIGS. 4 to 9). Therefore, it was confirmed that the composition comprising NKC or NRC can be effectively used as an active ingredient of anticancer agents.

The composition of the present invention may be a composition further comprising a pharmaceutically acceptable carrier.

The term "pharmaceutically acceptable", as used herein, refers to an amount sufficient for displaying a therapeutic effect but not causing side effects, and may be easily determined by those skilled in the art according to factors known in the medical field, including the type of illness, the patient's age, weight, health state, gender and sensitivity to drugs, administration routes, administration methods, administration frequency, treatment duration, and drugs used in combination or simultaneously. Generally, an active substance may be administered in a dose from about 5 mg/kg/day to 10 mg/kg/day. For oral administration, a dose ranging from 5 to 10 mg/kg may be suitable, and the dose may be administered one or more times per day.

The term "carrier", as used herein, refers to a carrier, excipient, or diluent that does not cause significant irritation to a subject and does not abrogate the biological activity and properties of the administered compound.

Examples of carriers, excipients, and diluents contained in the composition of the present invention may include lactose, dextrose, sucrose, sorbitol, mannitol, xylitol, erythritol, maltitol, starches, acacia rubber, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate and mineral oil.

Formulations suitable for the administration mode of the composition of the present invention are known, and typically, may include surfactants facilitating transport of drugs across a membrane. Such surfactants include derivatives of steroids, cationic lipids such as N-[1-(2,3-dioleyl)propyl]-N,N,N-trimethylammonium chloride (DOTMA), or cholesterol hemisuccinate.

In detail, the composition of the present invention may be used in a form of a general pharmaceutical preparation. Formulation for parenteral administration includes sterilized water solution, non-aqueous solution, suspension, emulsion, lyophilization preparation, or suppository. Propylene glycol, polyethylene glycol, vegetable oil such as olive oil, or injectable ester such as ethyloleate may be used as non-aqueous solution and suspension. Witepsol, macrogol, tween 61, cacao butter, laurin butter, glycerogelatin or the like may be used as suppository base. Additionally, the peptide may be used in a mixture with various pharmaceutically acceptable carriers such as physiological saline or organic solvents. Also, in order to increase the stability or absorptivity of the peptide, carbohydrates such as glucose, sucrose or dextran, antioxidants such as ascorbic acid or glutathione, chelating agents, low-molecular weight proteins or other stabilizers may be used. In addition, the peptide of the composition of the present invention may include a nucleic acid encoding the peptide to produce the peptide in a cell.

In another aspect, the present invention provides a method for preventing or treating cancer by administration of the composition to a subject.

The composition of the present invention is formulated into suitable preparations together with a pharmaceutically acceptable carrier, and then administered via various routes. The term "administration" means introduction of a predetermined amount of a substance into a patient by a certain suitable method, and the composition may be administered via any of the common routes, as long as it is able to reach a desired tissue. A variety of administration modes are contemplated, including intraperitoneally, intravenously, intramuscularly, subcutaneously, intradermally, orally, topically, intranasally, intrapulmonarily and intrarectally, but the present invention is not limited to these exemplified administration modes. However, since peptides are digested upon oral administration, active ingredients of a composition for oral administration should be coated or formulated for protection against degradation in the stomach. Also, the pharmaceutical composition of the present invention may be administered with the aid of a means for delivering the active ingredient into target cells. Preferred administration mode and preparation are intravenous injection, subcutaneous injection, intracutaneous injection, intramuscular injection or instillation. Injection preparations may be based on aqueous solvents, such as physiological saline or Ringer's solution, or non-aqueous solutions, such as vegetable oils, higher fatty acid esters (e.g., ethyl oleate, etc.), and alcohols (e.g., ethanol, benzyl alcohol, propylene glycol or glycerin) and may comprise pharmaceutically acceptable carriers, such as antiseptic stabilizers (e.g., ascorbic acid, sodium hydrogen sulfite, sodium pyrosulfite, BHA, tocopherol, EDTA, etc.), emulsifiers, pH-adjusting buffers, and/or anti-microbial preservatives (e.g., phenylmercuric nitrate, thimerosal, benzalkonium chloride, phenol, cresol, benzyl alcohol, etc.).

In still another aspect, the present invention provides use of the peptide represented by an amino acid sequence of the above Formula (I) in the preparation of the prophylactic or therapeutic agent for cancer.

Mode for the Invention

Hereinafter, the present invention will be described in detail with reference to the following Examples. However, these Examples are for illustrative purposes only, and the invention is not intended to be limited by these Examples.

Example 1

Synthesis of NKC and NRC Peptides and Effects on Normal Cell Survival in vitro

First, NKC and NRC peptides having the following amino acid sequences were synthesized.

```
                                      (SEQ ID NO. 1)
NKC:        APKAMKLLKKLLKLQKKGI-amine (SEQ ID NO. 2)
NRC:        APKAMRLLRRLLRLQKKGI-amide
```

In order to test toxicity of the synthesized NKC and NRC peptides on normal cells, each of the cultured human embryo fibroblast (FSF), human keratinocyte (HaCat) and human erythrocyte was treated with the synthesized peptide, and the viability of each cell was analyzed.

In detail, each $1 \times 10^4$ of FSF and HaCat cells was aliquoted to a 96-well plate, and cultured for 24 hrs. Subsequently, each of the synthesized peptides, a known anticancer peptide, buforin IIb, and a known non-cytotoxic peptide, magainin 2 was added thereto at a concentration of 10, 25, 50, 100 or 200 μg/ml, and then the cells were cultured for 4 days. Thereafter, MTT (3-[4,5-dimethylthiazol-2-yl]-2,5-diphenyltetrazolium bromide) was added, and color development was detected using a spectrophotometer to count the number of surviving cells. On the basis of this, viability of each cell was calculated (FIGS. 1 and 1*b*). In this connection, an experimental group treated with PBS only was used as a control group.

Meanwhile, PBS was added to erythrocytes obtained from the human blood, and diluted 1,000-fold. Each of the synthesized peptides, a known anticancer peptide, buforin IIb, and a known non-cytotoxic peptide, magainin 2 was added thereto at a concentration of 10, 25, 50, 100 or 200 μg/ml. After 30 min, disruption of erythrocytes was determined by the difference in absorbance using spectrometry (FIG. 3). In this connection, an experimental group treated with PBS only was used as a control group.

FIG. 1 is a graph showing the viability of FSF cells depending on treatment concentration of each peptide, FIG. 2 is a graph showing the viability of HaCat cells depending on treatment concentration of each peptide, and FIG. 3 is a graph showing the viability of erythrocytes depending on treatment concentration of each peptide. In FIGS. 1 to 3, (●) represents NKC, (▲) represents NRC, (■) represents buforin IIb, (▼) represents magainin 2, and (♦) represents PBS. As shown in FIGS. 1 to 3, unlike buforin IIb which remarkably reduced the cell viability above a predetermined concentration, the peptide of the present invention did not affect the viability of FSF cells, HaCat cells and erythrocytes even at the concentration of 200 μg/ml, indicating no effect on the viability of normal cells.

Example 2

Effects of NKC and NRC Peptides on Cancer Cell Survival in vitro

In order to test whether the peptides of the present invention found to show no effect on the viability of normal cells exhibit toxicity on cancer cells, each of human malignant melanoma cell line (SK-MEL-5), human cervical adenocarcinoma cell line (HeLa), human colon carcinoma cell line (HCT-116), human lung adenocarcinoma cell line (NCI-H23), human erythroleukemia cell line (K-562) and human prostate cancer cell line (PC3) were treated with the peptides of the present invention, and the viability of each cell line was analyzed.

Figure 4:
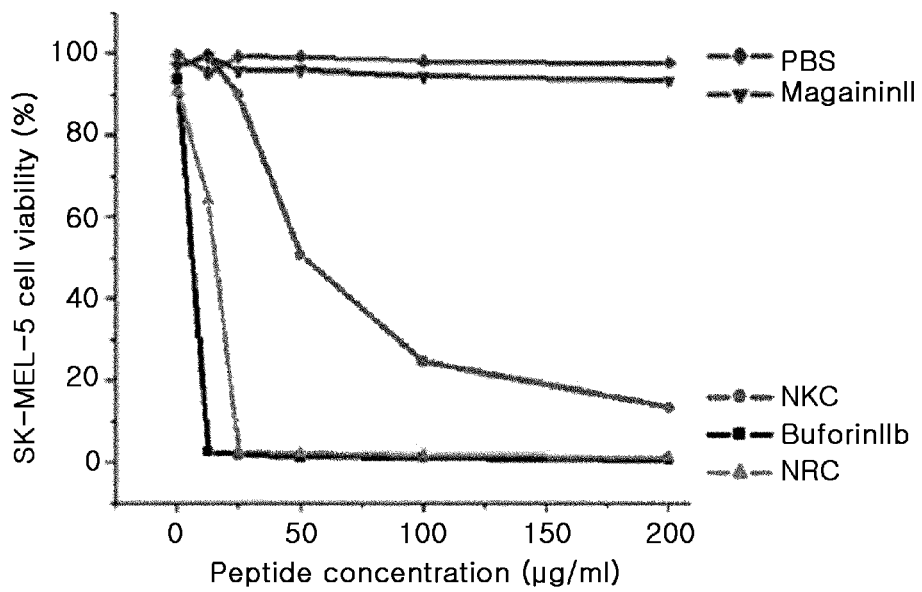
FIG. 4 is a graph showing the viability of SK-MEL-5 cell line depending on the treatment concentration of the peptide.
Figure 9:
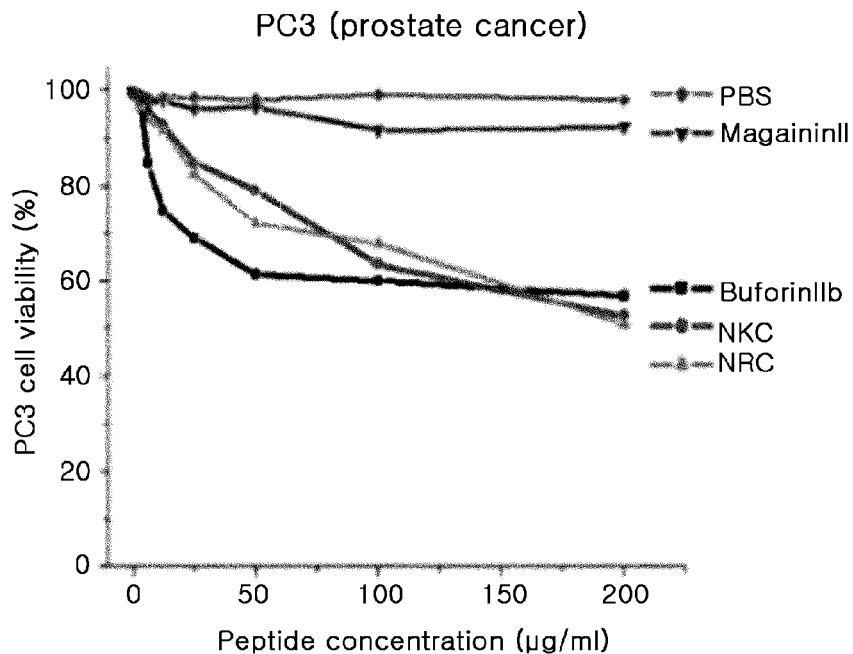
FIG. 9 is a graph showing the viability of PC3 cell line depending on the treatment concentration of the peptide.

In detail, each $1 \times 10^4$ of SK-MEL-5 cell line, HeLa cell line, HCT-116 cell line, NCI-H23 cell line, K-562 cell line and PC3 cell line was aliquoted to a 96-well plate, and cultured for 24 hrs. Subsequently, each of the synthesized peptides, buforin IIb, and magainin 2 was added thereto at a concentration of 10, 25, 50, 100 or 200 μg/ml, and then the cells were cultured for 4 days. Thereafter, MTT was added, and color development was detected using a spectrophotometer to count the number of surviving cells. On the basis of this, the viability of each cell was calculated (FIGS. 4 and 9). In this connection, an experimental group treated with PBS only was used as a control group.

Figure 5:
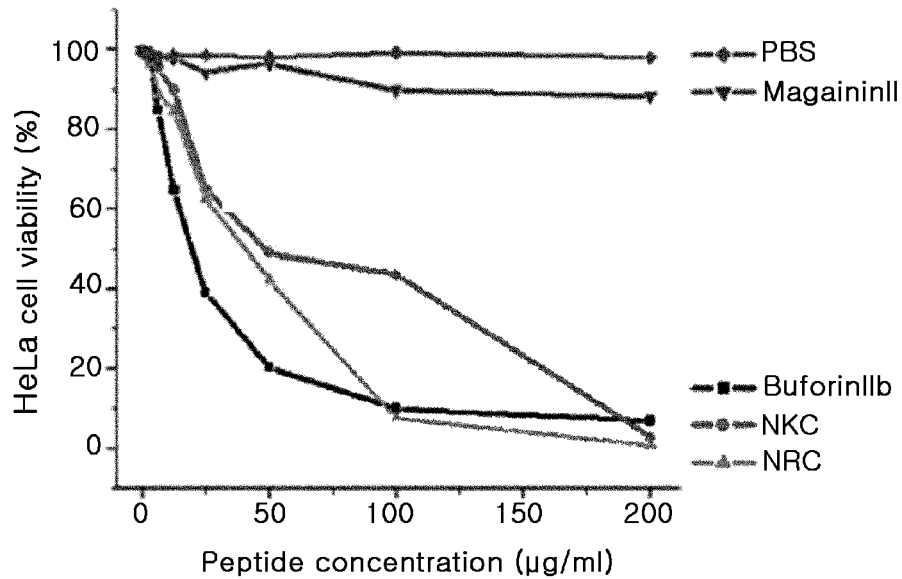
FIG. 5 is a graph showing the viability of HeLa cell line depending on the treatment concentration of the peptide.
Figure 6:
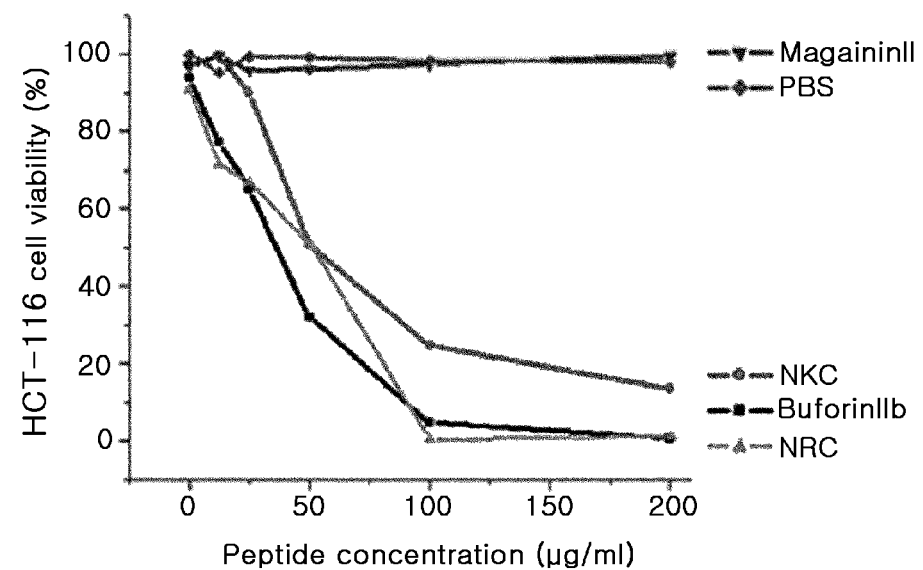
FIG. 6 is a graph showing the viability of HCT-116 cell line depending on the treatment concentration of the peptide.
Figure 7:
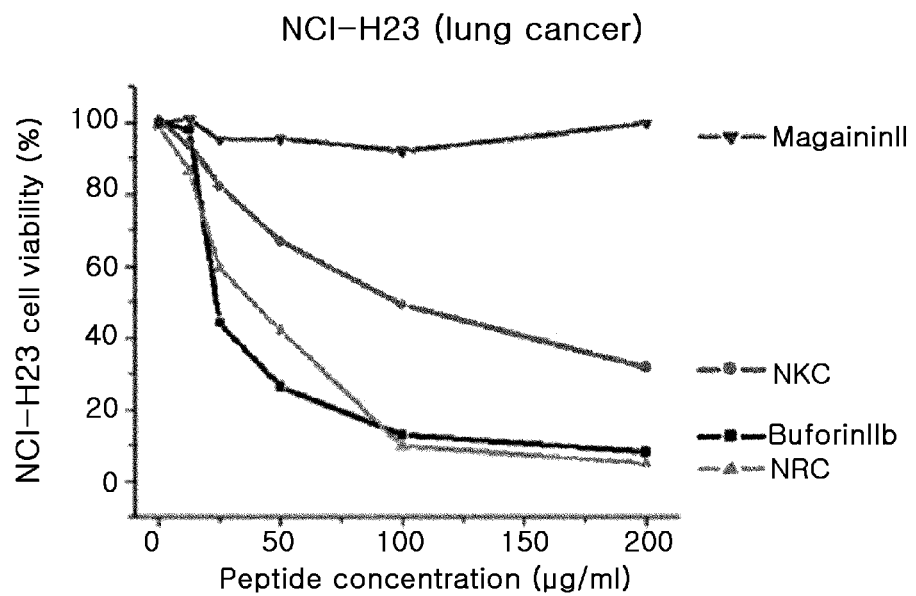
FIG. 7 is a graph showing the viability of NCI-H23 cell line depending on the treatment concentration of the peptide.
Figure 8:
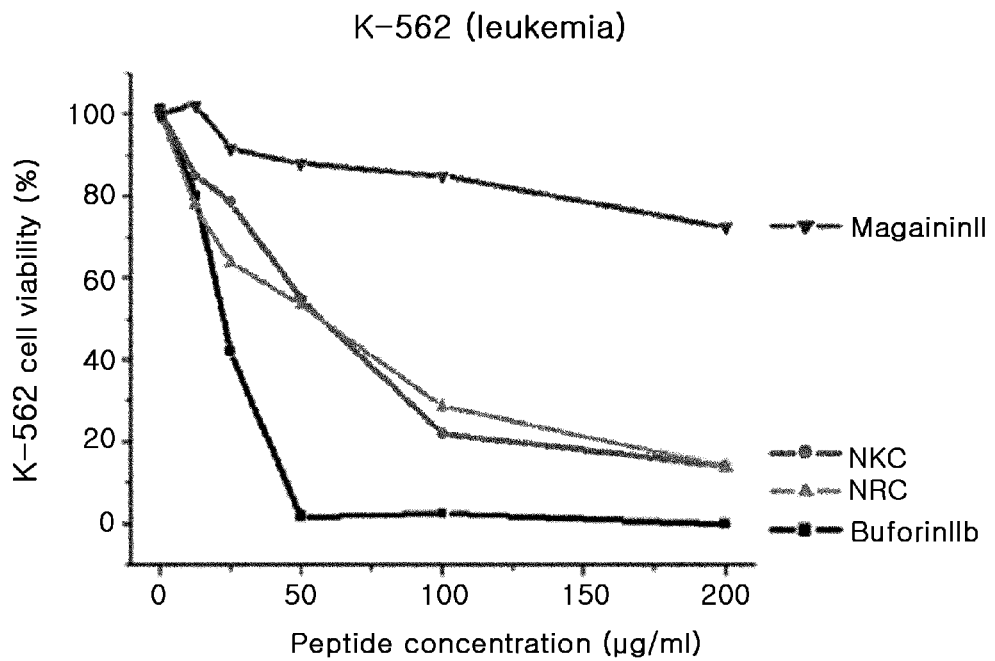
FIG. 8 is a graph showing the viability of K-562 cell line depending on the treatment concentration of the peptide.

FIG. 4 is a graph showing the viability of SK-MEL-5 cell line depending on treatment concentration of each peptide, FIG. 5 is a graph showing the viability of HeLa cell line depending on treatment concentration of each peptide, FIG. 6 is a graph showing the viability of HCT-116 cell line depending on treatment concentration of each peptide, FIG. 7 is a graph showing the viability of NCI-H23 cell line depending on treatment concentration of each peptide, FIG. 8 is a graph showing the viability of K-562 cell line depending on treatment concentration of each peptide, and FIG. 9 is a graph showing the viability of PC3 cell line depending on treatment concentration of each peptide. In FIGS. 4 to 9, (●) represents NKC, (▲) represents NRC, (■) represents buforin IIb, (▼) represents magainin 2, and (♦) represents PBS. As shown in FIGS. 4 to 9, it was confirmed that the peptides of the present invention were able to kill all of the cell lines at the concentration ($IC_{50}$) of 5 to 40 μg/ml.

Accordingly, it can be seen that the peptides of the present invention exhibit cell selectivity of showing cytotoxicity on cancer cells and no cytotoxicity on normal cells.

Example 3

Cancer Cell Selectivity of NKC and NRC Peptides

To reconfirm the cell selectivity of the peptides of the present invention, each $2 \times 10^5$ of normal FSF and HaCat cells, and SM-MEL-5 cell line, HeLa cell line and HCT-116 cell line as cancer cells were cultured at 37° C. overnight, and FITC (fluorescein isothiocyanate)-labeled peptides, buforin IIB and magainin 2 were added thereto at a concentration of 20 μg/ml, followed by incubation for 1 hr. Each cell or cell line was washed with PBS, and observed under a fluorescence microscope (FIG. 10).

Figure 10:
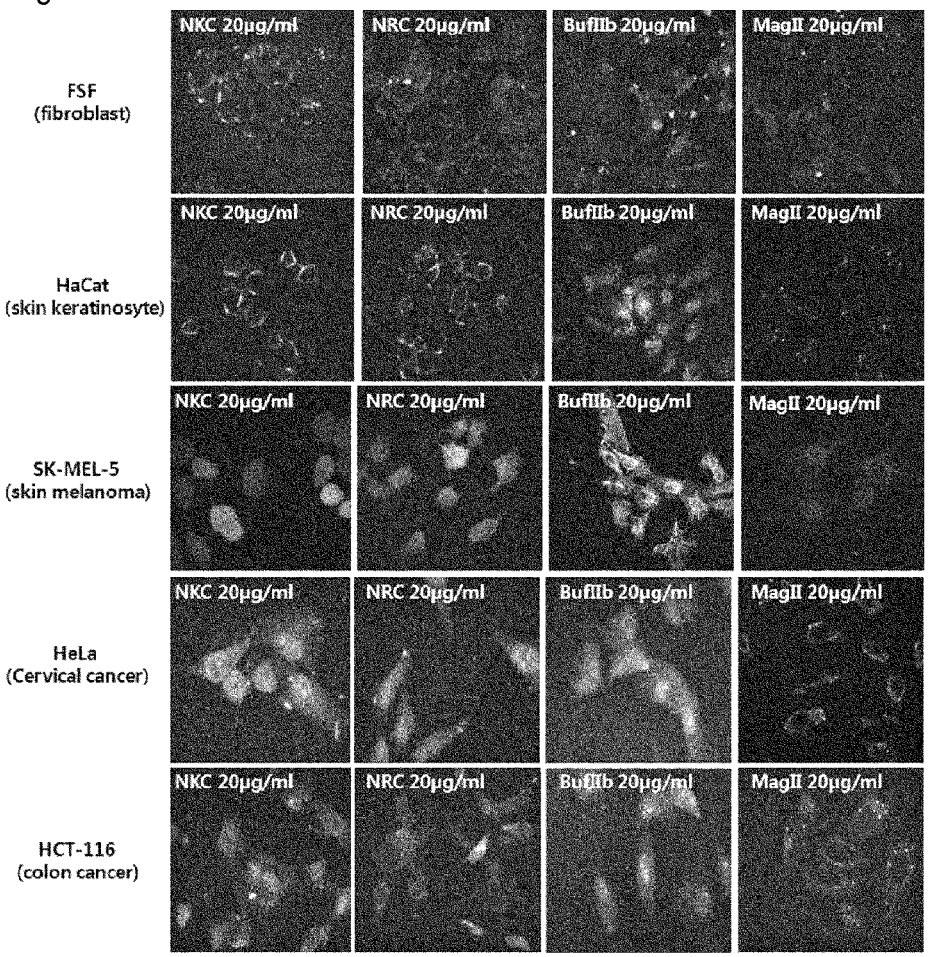
FIG. 10 is a fluorescent microscopic photograph showing cell selectivity of the peptide of the present invention.

FIG. 10 is a fluorescent microscopic photograph showing cell selectivity of the peptide of the present invention. As shown in FIG. 10, the peptides of the present invention were rarely detected in the normal FSF and HaCat cells, but detected in the cancer cells, SM-MEL-5 cell line, HeLa cell line and HCT-116 cell line in a large quantity, whereas buforin IIb were rarely detected in the normal FSF cells, but detected in normal HaCat cells at a predetermined level, and detected in the cancer cells, SM-MEL-5 cell line, HeLa cell line and HCT-116 cell line in a large quantity. Magainin 2 was not detected in all normal cells and cancer cells. It can be seen that the peptides of the present invention exhibit excellent cancer cell selectivity, compared to buforin IIb and magainin 2 showing little cell selectivity or no cell selectivity.

Example 4

Concentration Dependence of Anticancer Activity of NKC and NRC Peptides

From the results of Example 3, it was confirmed that the peptides of the present invention exhibited cancer cell selectivity. It will be tested whether the peptides of the present invention exhibit anticancer activity in a concentration-dependent manner.

In detail, each $1 \times 10^5$ of normal FSF cells and K-562 cancer cell line were cultured for 24 hrs, and treated with each of FITC (fluorescein isothiocyanate)-labeled peptides and buforin IIB at a concentration of 0, 10 or 20 μg/ml, followed by incubation for 1 hr. Each of the cultured cell or cell line was analyzed by flow cytometry (FIGS. 11 and 12).

Figure 11:
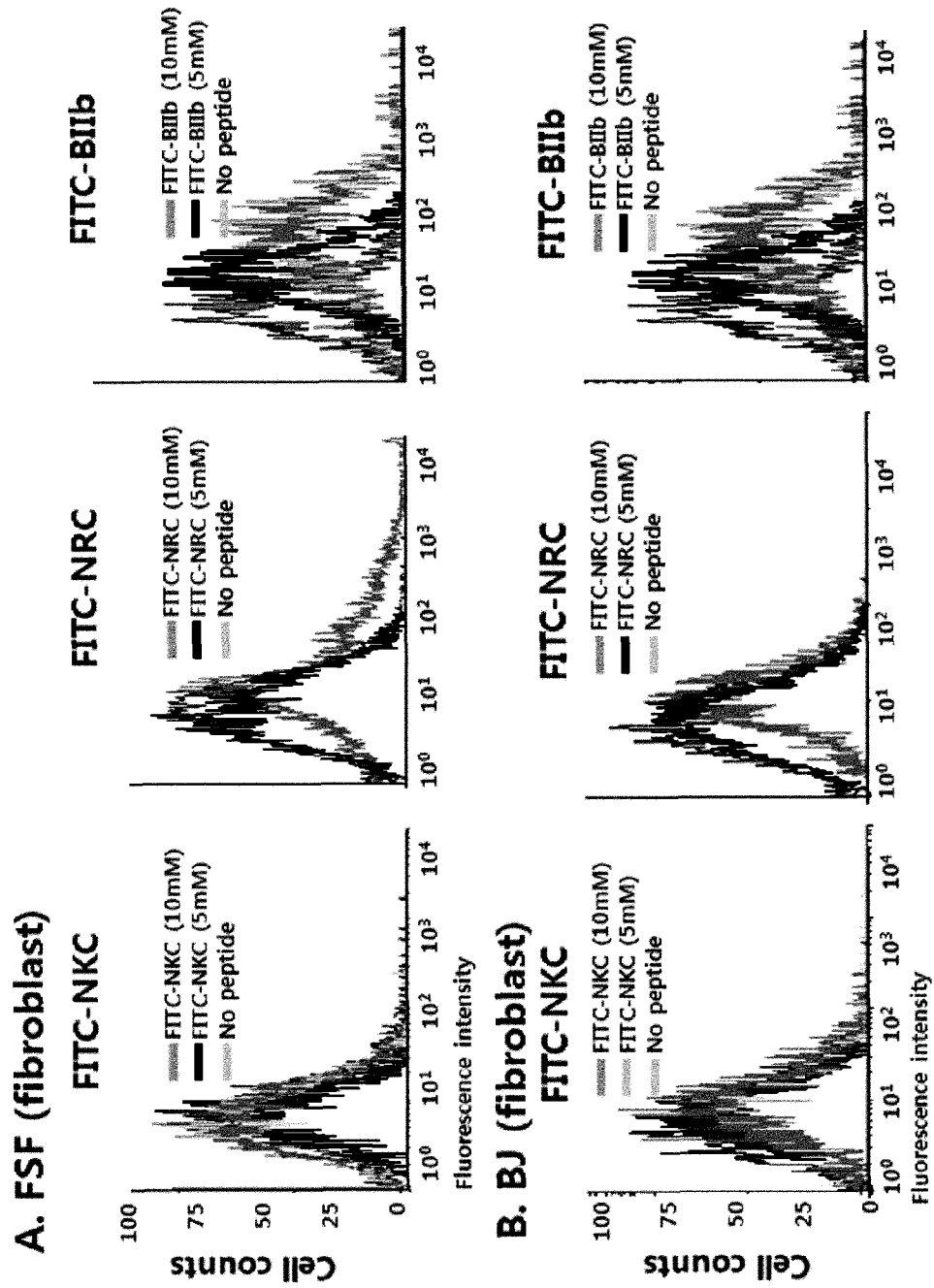
FIG. 11 is a graph showing the effect of the peptide of the present invention on normal cells depending on the treatment concentration.
Figure 12:
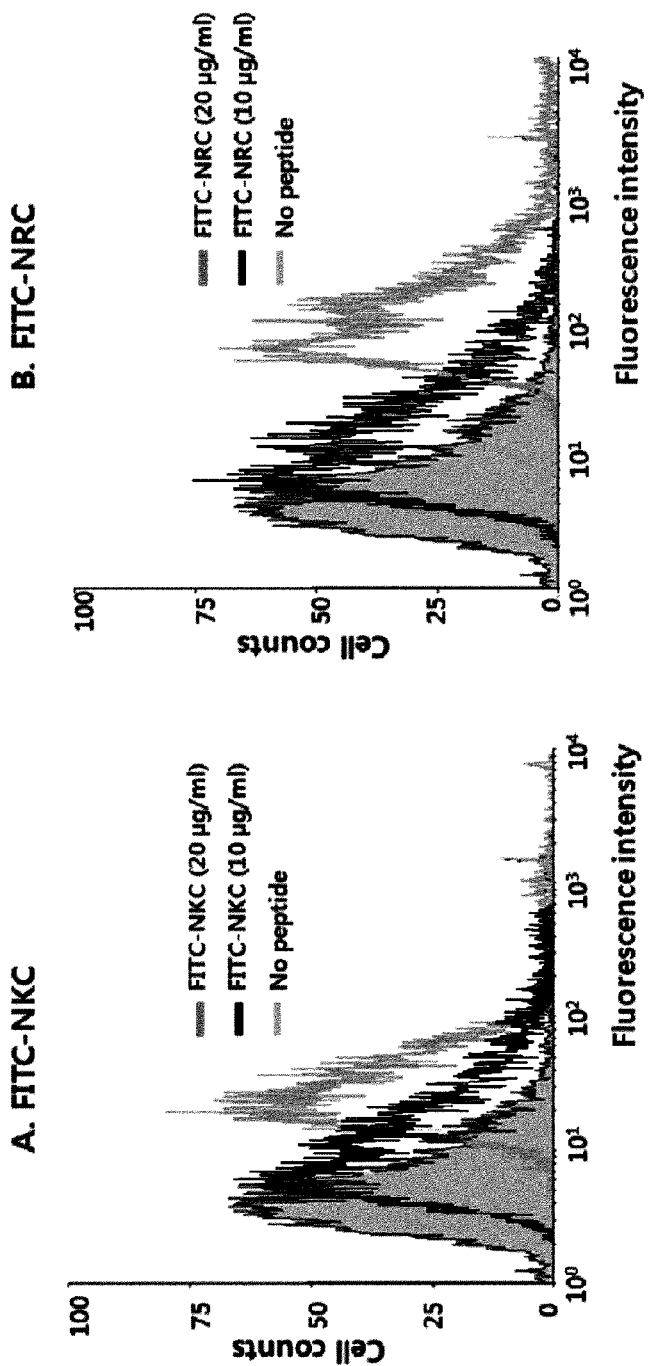
FIG. 12 is a graph showing the effect of the peptide of the present invention on cancer cells depending on the treatment concentration.

FIG. 11 is a graph showing the effect of the peptide of the present invention on normal cells depending on treatment concentration, and FIG. 12 is a graph showing the effect of the peptide of the present invention on cancer cells depending on treatment concentration. As shown in FIGS. 11 and 12, the normal FSF cells were not affected even though varying the treatment concentration of the peptide of the present invention. On the contrary, the reactivity of the peptide of the present invention against K-562 cancer cell line increased, as its treatment concentration was increased. Accordingly, it can be seen that the peptides of the present invention exhibit anticancer activity against cancer cells in a concentration-dependent manner.

Example 5

Cell Surface Molecules Affecting Anticancer Activity of NKC and NRC Peptides

As shown in the results of Example 3, the peptides of the present invention exhibited cancer cell selectivity. To demonstrate cell selectivity, many studies have been made. Consequently, it was assumed that cell selectivity is caused by the charge of the peptides of the present invention and the surface charge of cancer cells. In detail, the peptides of the present invention have an overall positive charge, normal cells have an overall neutral charge on the cell surface, whereas cancer cells have an overall negative charge on the cell surface due to higher distribution of the negatively charged cell surface molecules, ganglioside, phosphatidylserine, and heparin. Thus, the present inventors suggested that the cell selectivity of the peptides of the present invention is attributed to their positive charge, which more attracts the negative surface charge on cancer cells than the neutral surface charge on normal cells.

Accordingly, the present inventors assumed that external addition of ganglioside, phosphatidylserine, and heparin to the cancer cell culture media causes dispersion of the peptides of the present invention in the cancer cell surface and the negatively charged materials added to the culture media, whereby the anticancer activity is reduced by the addition of negatively charged materials in a concentration-dependent manner. To demonstrate this assumption, a competitive binding assay was performed using ganglioside, phosphatidylserine or heparin.

In detail, the K-562 cancer cell line was aliquoted to each well of 96-well plate at a density of $1 \times 10^4$, and each well was treated with 1 to 100 μg/ml of heparin, phosphatidylserine or ganglioside, and 10 μg/ml of the peptides of the present invention, buforin IIb and magainin 2, followed by cultivation for 48 hrs. Cell viability was measured in the same manner as in Example 1 (MTT assay) (FIGS. 13 to 15).

Figure 13:
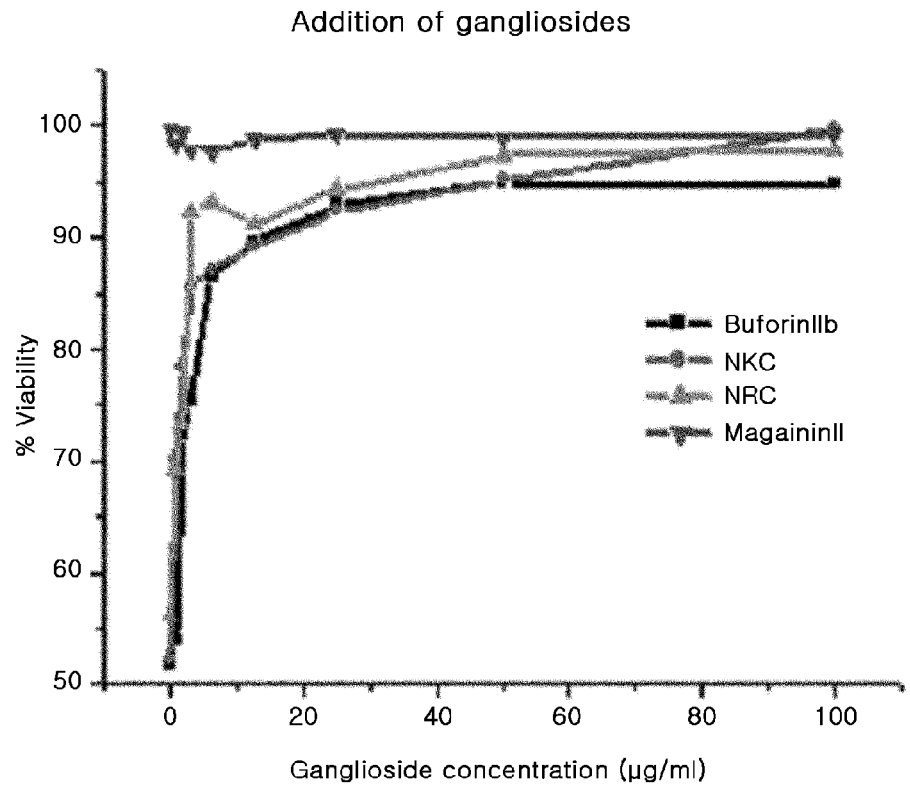
FIG. 13 is a graph showing the changes in anticancer activity of each peptide depending on the treatment concentration of ganglioside.
Figure 14:
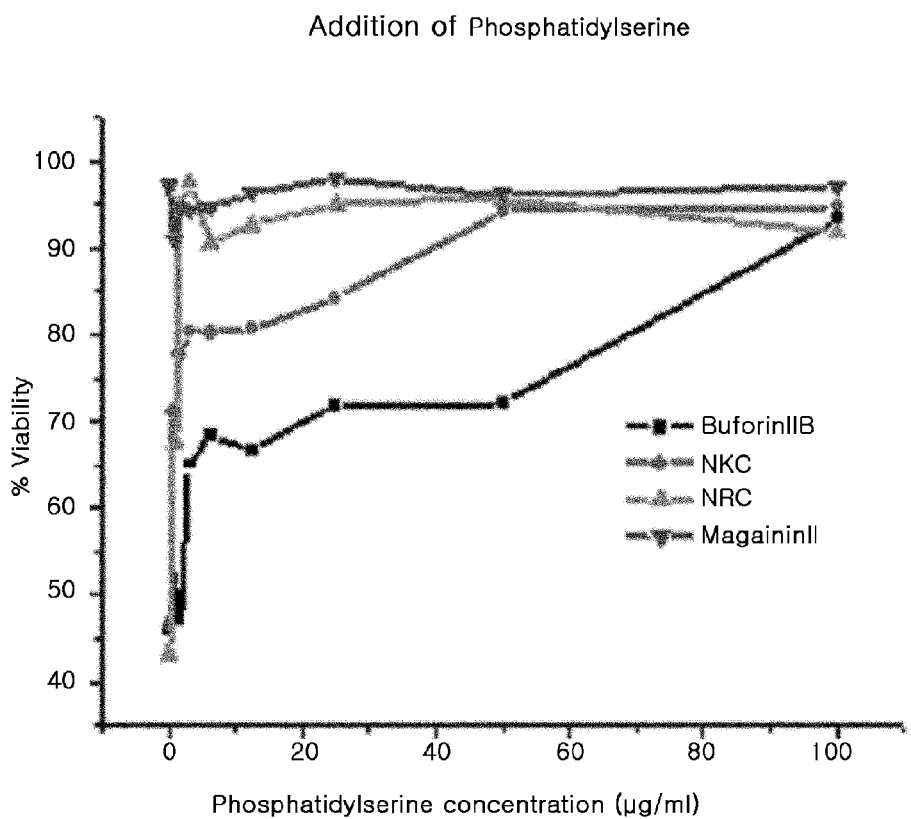
FIG. 14 is a graph showing the changes in anticancer activity of each peptide depending on the treatment concentration of phosphatidylserine.
Figure 15:
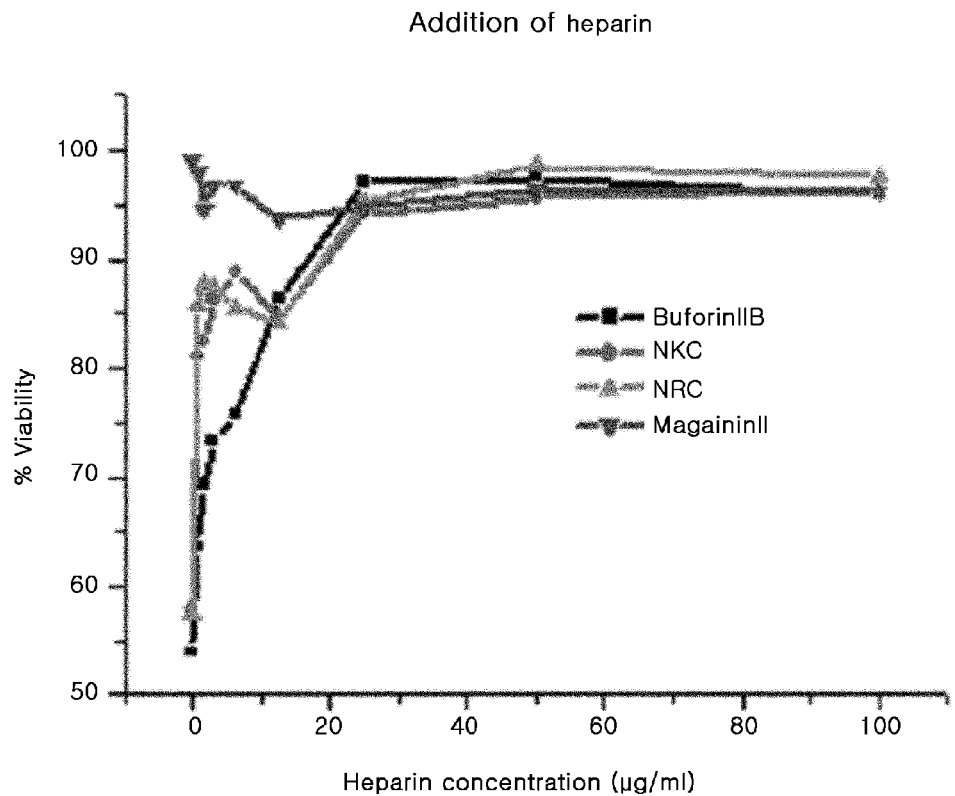
FIG. 15 is a graph showing the changes in anticancer activity of each peptide depending on the treatment concentration of heparin.

FIG. 13 is a graph showing the changes in anticancer activity of each peptide depending on treatment concentration of ganglioside, FIG. 14 is a graph showing the changes in anticancer activity of each peptide depending on treatment concentration of phosphatidylserine, and FIG. 15 is a graph showing the changes in anticancer activity of each peptide depending on treatment concentration of heparin. In FIGS. 13 to 15, (●) represents NKC, (▲) represents NRC, (■) represents buforin IIb, and (▼) represents magainin 2. As shown in FIGS. 13 to 15, it was found that cancer cells treated with the peptides of the present invention and buforin IIb showed high cell viability by the external addition of ganglioside, phosphatidylserine or heparin.

The results of FIGS. 13 to 15 suggest that the cancer cell selectivity of the peptides of the present invention is attributed to their charge, which attracts the surface charge of cancer cells.

Example 6

Anticancer Activity of NKC and NRC Peptides on Cancer Cells Lacking Ganglioside

From the results of Example 5, it was confirmed that the cancer cell selectivity of the peptides of the present invention is attributed to their charge, which attracts the surface charge of cancer cells, which will be demonstrated by the following experiment.

The above results suggested that the cancer cell selectivity of the peptides of the present invention is directly caused by the cell surface molecules present on cancer cell surface such as ganglioside. Thus, it can be assumed that in the absence of ganglioside on the cancer cell surface, the peptides of the present invention will not exhibit the effective anticancer activity. To demonstrate this assumption, a competitive binding assay was performed using an inhibitor of ganglioside biosynthesis, PMPP (1-phenyl-2-palmitoylamino-3-morpholino-1-propanol).

In detail, the K-562 cancer cell line was aliquoted to each well of 96-well plate at a density of $1 \times 10^4$, and each well was treated with an inhibitor of ganglioside biosynthesis, PMPP at the concentration of 0, 2 and 4 μM, and then treated with 10 μg/ml of the peptides of the present invention, buforin IIb and magainin 2, followed by cultivation for 48 hrs. Cell viability was measured in the same manner as in Example 1 (MTT assay) (FIG. 16).

Figure 16:
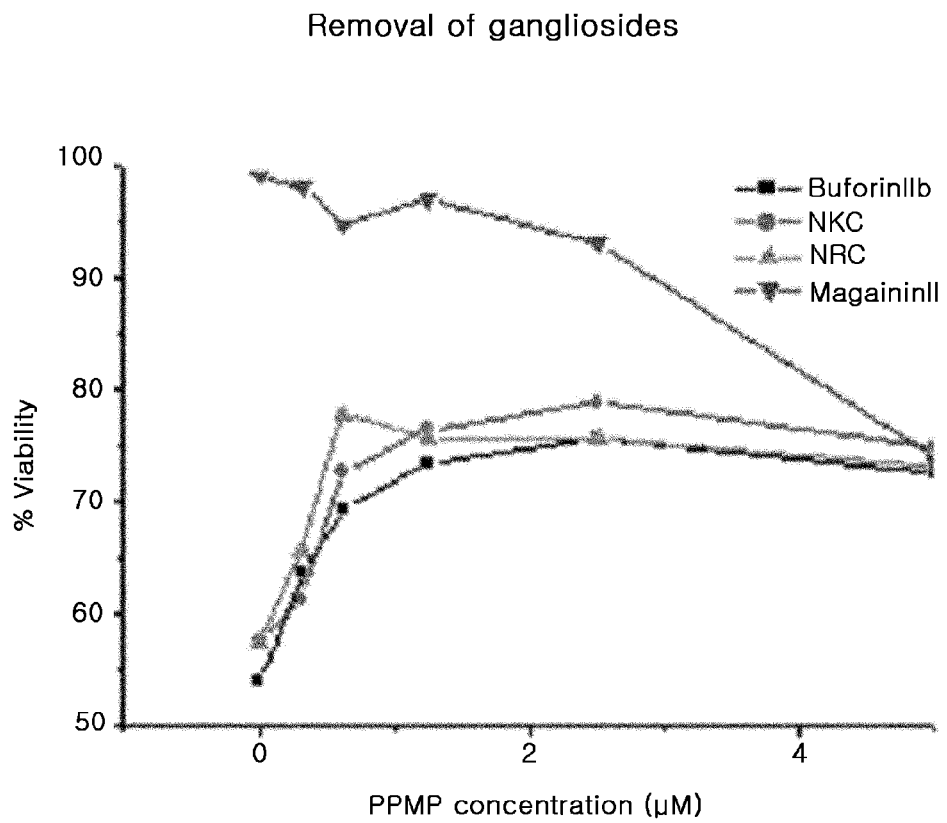
FIG. 16 is a graph showing the changes in anticancer activity of each peptide in cancer cells which lack ganglioside.

FIG. 16 is a graph showing the changes in anticancer activity of each peptide depending on treatment concentration of PMPP in cancer cells which lack ganglioside, in which (●) represents NKC, (▲) represents NRC, (■) represents buforin IIb, and (▼) represents magainin 2. As shown in FIG. 16, it was found that the viability of cancer cells treated with the peptides of the present invention and buforin IIb was increased, as ganglioside biosynthesis in cancer cells is inhibited by increasing concentration of the inhibitor of ganglioside biosynthesis, suggesting that the cell selectivity of the peptides of the present invention or buforin IIb was reduced with a reduced content of ganglioside on the cancer cell surface, leading to a reduction in the anticancer activity.

Accordingly, it is apparent that the cancer cell selectivity of the peptides of the present invention is attributed to their charge, which attracts the surface charge of cancer cells.

Example 7

Inhibitory Effect of Ganglioside on Anticancer Activity of NKC and NRC Peptides

From the results of Examples 5 and 6, it was confirmed that the anticancer activity of the peptides of the present invention are directly affected by ganglioside present on the surface of cancer cells, which will be reconfirmed by flow cytometry.

Figure 17:
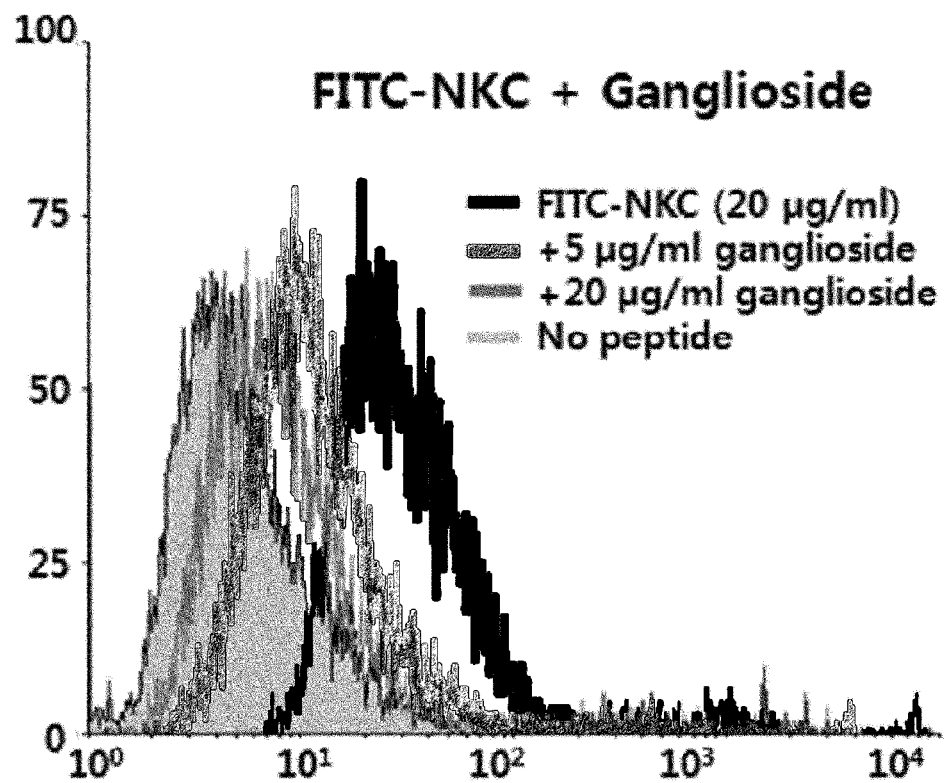
FIG. 17 is a graph showing the effect of the peptide NKC of the present invention on cancer cells depending on the treatment concentration of ganglioside.
Figure 18:
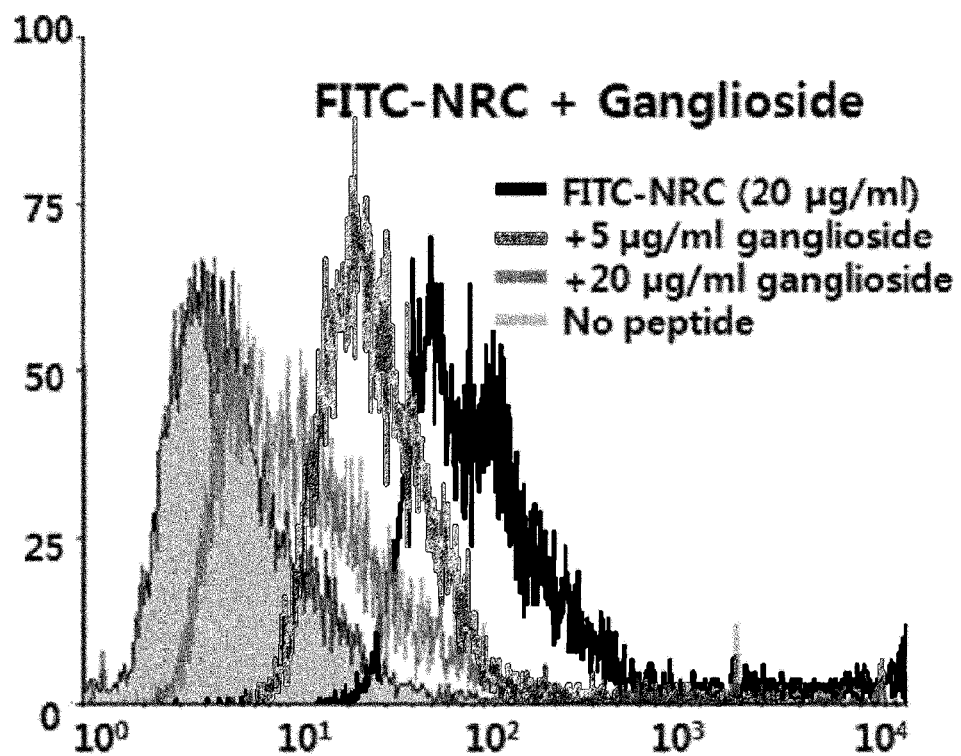
FIG. 18 is a graph showing the effect of the peptide NRC of the present invention on cancer cells depending on the treatment concentration of ganglioside.

In detail, each $1 \times 10^5$ of K-562 cancer cell line was cultured for 24 hrs, and treated with the FITC (fluorescein isothiocyanate)-labeled peptides of the present invention (20 μg/ml) and 0, 5 or 20 μg/ml of ganglioside, followed by cultivation for 1 hr. Each of the cultured cell line was analyzed by flow cytometry (FIGS. 17 and 18). In this connection, cell line cultured without treatment of the peptides of the present invention and ganglioside was used as a control group.

FIG. 17 is a graph showing the effect of the peptide NKC of the present invention on cancer cells depending on treatment concentration of ganglioside, and FIG. 18 is a graph showing the effect of the peptide NRC of the present invention on cancer cells depending on treatment concentration of ganglioside. As shown in FIGS. 17 and 18, it was found that the anticancer activity of the peptides of the present invention was inhibited, as the addition of ganglioside was increased. These results suggest that ganglioside present on the surface of cancer cell and externally added ganglioside competitively act on the peptides of the present invention, whereby the anticancer activity of the peptides of the present invention was reduced by externally added ganglioside in a concentration-dependent manner.

Accordingly, it was reconfirmed that the anticancer activity of the peptides of the present invention is directly affected by ganglioside present on the surface of cancer cells.

The invention claimed is:

1. A method for treating a cancer cell line in vitro, comprising the step of treating a cancer cell line with a peptide which is represented by SEQ ID NO. 1 or SEQ ID NO. 2, wherein the cancer cell line is a skin cancer, cervical cancer, lung cancer, rectal cancer, prostate cancer, or hematologic malignancies cell line.

2. The method according to claim 1, wherein the peptide retains a stable activity at a high salt concentration due to a capping motif contained at N- and C-terminus.

3. The method according to claim 1, wherein the peptide is administered together with a pharmaceutically acceptable carrier.

* * * * *